US005874220A

United States Patent [19]

Fach et al.

[11] Patent Number: 5,874,220

[45] Date of Patent: Feb. 23, 1999

[54] **PRIMERS FOR THE AMPLIFICATION OF GENES CODING FOR THE ENTEROTOXIN AND THE LECITHINASE OF *CLOSTRIDIUM PERFRINGENS* AND THEIR APPLICATION TO THE DETECTION AND NUMERATION OF THESE BACTERIAE**

[75] Inventors: Patrick Fach, Creteil; Jean-Pierre Guillou, deceased, late of Chennevieres, by Raymond Guillou, legal representative; Michel Popoff, Clamart, all of France

[73] Assignees: Institut Pasteur; Centre National D'Etudes Verterinaires et Alimentairescneva, both of France

[ * ] Notice: The term of this patent shall not extend beyond the expiration date of Pat. No. 5,538,851.

[21] Appl. No.: 666,405

[22] PCT Filed: Dec. 22, 1994

[86] PCT No.: PCT/EP94/04292

§ 371 Date: Nov. 8, 1996

§ 102(e) Date: Nov. 8, 1996

[87] PCT Pub. No.: WO95/17521

PCT Pub. Date: Jun. 29, 1995

Related U.S. Application Data

[63] Continuation-in-part of Ser. No. 172,026, Dec. 22, 1993, Pat. No. 5,538,851.

[51] Int. Cl.[6] .............................. C12Q 1/68; C12P 19/34; C07H 21/04

[52] U.S. Cl. .......................... 435/6; 435/91.2; 435/320.1; 536/23.7

[58] Field of Search .......................... 435/6, 91.2, 320.1; 536/24.33, 24.32, 23.7

[56] References Cited

FOREIGN PATENT DOCUMENTS

| | | |
|---|---|---|
| 395292 | 10/1990 | European Pat. Off. . |
| 409159A2 | 1/1991 | European Pat. Off. . |
| 03049699 | 4/1991 | Japan . |

OTHER PUBLICATIONS

Saito et al., *Int. J. Food Microbiol.* 17(1), 47–55 (1992).
Havard et al., *FEMS Microbiol. Lett.* 97, 77–82 (1992).
Saint–Joanis et al., *Mol. Gen. Genet.* 219, 453–460 (1989).
Czeczulin et al., *Infec. Immun.* 61(8), 3429–3439(1993).
Fach et al., J. Appl. Bacteriol. 74,61–68 (01 Jan. 1993).
Fach et al, J. Appl. Bacteriol, (1993 Jan.) 74 pp.61–66.
Daude, et al, J. Appl. Bacteriol, (1994 Dec) 77 pp.650–655.
Titball et al, Infection and Immunity, vol. 57, No. 2, Feb. 1989 pp. 367–376.
Okabe et al, Biochem. Biophys. Res. Commun. vol. 160 (1989) pp. 33–39.
Leslie et al, Mol. Microbiol. 3:383–392 (1989).
Fach et al, Med. Mal. Infect., (1993) 23/2 (70–77).

*Primary Examiner*—Kenneth R. Horlick
*Attorney, Agent, or Firm*—Bierman, Muserlian and Lucas

[57] ABSTRACT

Primers selected from the group consisting of SEQ ID Nos. 1, 2, 3, 4, 5, 6, 7 and 8 and an isolated nucleic acid encoding the *C. Perfringens* type β-toxin $\beta_2$ consisting of nucleotide sequence of SEQ ID No. 27 and the plasmids of the gene thereof.

4 Claims, 5 Drawing Sheets

```
peptide 21  (N)- Y - D - I - N - T - V - V - N - I - S - E - D - E
P221           5'-TAT GAT ATI AAT ACI GTI GTI AAT ATI TCI GAA GAT GAA-3'

peptide 23     V - M - E - N - Y - L - N - A - L - K Y - I - L - T - P - S - F
               GTI ATG GAA AAT TAT TTI AAT GCI TTI AAA
p263        3'-CAI TAC CTT TTA ATA AAI TTA CGI AAI TT-5'

N-terminal     K - E - I - D - A - Y - R - K - V - M - E - N - Y - L - N - A - L
p268        5'-AAA GAA ATI GAT GCI TAT AGI AAA GTI ATG GAA AAT TAT TTI AAT GC-3'
p279        5'-AAA GAA ATI GAT GCI TAT AGI AAA GTI ATG G-3'

peptide 13     N - F - T - P - A - S - I
               AAT TTI ACI CCI GCI TCI AT
p280        3'-TTA AAA TGI GGI CGI AGI TA-5'
```

FIG. 2

```
1     AAA GAA ATG GAT GCG TAT AGG AAA GTG ATG GAG AAT TAT CTT AAT GCT   48
1      K   E   M   D   A   Y   R   K   V   M   E   N   Y   L   N   A    16

49    TTA AAA AAC TAC GAT ATT AAT ACA GTT GTA AAC ATT TCA GAA GAT GAA   96
17     L   K   N   Y   D   I   N   T   V   V   N   I   S   E   D   E    32

97    AGA GTA AAT AAT GTT GAA CAG TAT AGA GAA ATG TTA GAA GAT TTT AAA  144
33     R   V   N   N   V   E   Q   Y   R   E   M   L   E   D   F   K    48

145   TAT GAT CCT AAC CAA CAA CTG AAA TCT TTT GAA ATA CTT AAT TCA CAA  192
49     Y   D   P   N   Q   Q   L   K   S   F   E   I   L   N   S   Q    64

193   AAG AGC GAT AAT AAA GAA ATA TTT AAT GTA AAA ACT GAA TTT TTA AAT  240
65     K   S   D   N   K   E   I   F   N   V   K   T   E   F   L   N    80

241   GGT GCA ATT TAT GAT ATG GAA TTT ACT GTA TCA TCT AAA GAT GGA AAA  288
81     G   A   I   Y   D   M   E   F   T   V   S   S   K   D   G   K    96

289   TTA ATA GTA TCT GAT ATG GAA AGA ACA AAA GTT GAG AAT GAA GGA AAA  336
97     L   I   V   S   D   M   E   R   T   K   V   E   N   E   G   K   112

337   TAT ATT TTA ACA CCA TCA TTT AGA ACT CAA GTT TGT ACA TGG GAT GAT  384
113    Y   I   L   T   P   S   F   R   T   Q   V   C   T   W   D   D   128

385   GAA CTA GCA CAA GCA ATT GGG GGA GTT TAT CCA CAA ACA TAT TCT GAT  432
129    E   L   A   Q   A   I   G   G   V   Y   P   Q   T   Y   S   D   144

433   AGA TTT ACA TAT TAT GCA GAT AAT ATA TTA TTA AAC TTC AGA CAA TAT  480
145    R   F   T   Y   Y   A   D   N   I   L   L   N   F   R   Q   Y   160
```

FIG. 3A

```
481   GCA ACT TCA GGT TCA AGA GAT TTA AAA GTA GAA TAT AGT GTT GTA GAT   528
161    A   T   S   G   S   R   D   L   K   V   E   Y   S   V   V   D    176

529   CAT TGG ATG TGG AAA GAT GAT GTT AAA GCT TCT CAA ATG GTA TAT GGT   576
177    H   W   M   W   K   D   D   V   K   A   S   Q   M   V   Y   G    192

577   CAA AAT CCT GAT TCT GCT AGA CAA ATA AGA TTA TAT ATA GAA AAA GGA   624
193    Q   N   P   D   S   A   R   Q   I   R   L   Y   I   E   K   G    208

625   CAA TCT TTC TAT AAA TAT AGA ATA AGA ATT AAA AAC TTT ACA CCT GCA   672
209    Q   S   F   Y   K   Y   R   I   R   I   K   N   F   T   P   A    224

673   TCA ATT AGA GTA TTT GGT GAA GGG TAT TGT GCA TAG AAA AAA ATA TGA   720
225    S   I   R   V   F   G   E   G   Y   C   A   *                    236

721   AGT GAC TTA GTC ACT TCA TAT TTT TTT TAC TAT TAA TTT TAT TAT ATA   768

769   AAA ACC TAA CAT ACA TGA AAG TAT TCT TAA TAC AGT TAT ATC AAA ATT   816

817   AAA GTA GGG GAA ATA AAA TAA AAG GCT AAA AAC TAT ATT AAA AAC TAT   864

865   AAA AAT TAT TAA ATT AGC                                           882
```

FIG. 3B

```
    Gap Weight:  3.000          Average Match: 0.540
 Length Weight:  0.100        Average Mismatch: -0.396
       Quality:   73.4        Length:   338
         Ratio:  0.326         Gaps:    5
Percent Similarity: 38.117    Percent Identity: 15.695

                   .         .         .         .         .
  1 ...............................KEMDAYRKVMENYLNALKN 19
                                     |. .  |   .: .. :..
  1 MKKKFISLVIVSSLLNGCLLSPTLVYANDIGKTTTITRNKTSDGYTIITQ 50
                   .         .         .         .         .
 20 YDINTVVNISEDERVNNVEQY......REMLEDFKYDPNQQLKSFEILNS 63
          | ..:    | |.. .| :.:      | : :.:. : .  :.  :::.|
 51 NDKQIISYQSVDSSSKNEDGFTASIDARFIDDKYSSEMTTLINLTGFMSS 100
                   .         .         .         .         .
 64 QKSDNKEIFNV...............KTEFLNGAIYD............. 85
        .|.|  . :|:               ...:||:.| :
101 KKEDVIKKYNLHDVTNSTAINFPVRYSISILNESINENVKIVDSIPKNTI 150
                   .         .         .         .         .
 86 ....MEFTVSSKDGKLIVSDMERTKVENEGKYILTPSF............ 119
            :. |:: | |  |  : ::.|.. |:.|  ...:
151 SQKTVSNTMGYKIGGSIEIEENKPKASIESEYAESSTIEYVQPDFSTIQT 200
                   .         .         .         .         .
120 ..RTQVCTWDDELAQAIGGVYPQTYSDRFTYYADNILLNFRQYATSGSRD 167
          .|  ..||..:.:..  | |  . .:..  |:::::: |  ...:. :
201 DHSTSKASWDTKFTETTRGNYNLKSNNPV..YGNEMFMYGRYTNVPATEN 248
                   .         .         .         .         .
168 LKVEYSVVDHWMWKDDVKASQMVYGQNPDSARQIRLYIEKGQSFYKYRIR 217
        : .:| : .      :.. | :: :.|..... |:: :|::.. | .. .
249 IIPDYQMSKLITGGLNPNMSVVLTAPNGTEESIIKVKMERERNCYYLNWN 298
                   .         .         .
218 IKNFTPAS.............................. 225
          |:...
299 GANWVGQVYSRLAFDTPNVDSHIFTFKINWLTHKVTAI 336
```

FIG. 4

PRIMERS FOR THE AMPLIFICATION OF GENES CODING FOR THE ENTEROTOXIN AND THE LECITHINASE OF *CLOSTRIDIUM PERFRINGENS* AND THEIR APPLICATION TO THE DETECTION AND NUMERATION OF THESE BACTERIAE

This application is a continuation-in-part of Ser. No. 08/172,026, filed Dec. 22, 1993, Pat. No. 5,538,851.

The present invention relates to primers for the amplification of genes coding for the enterotoxin and the lecithinase, also called phospholipase C, of *Clostridium perfringens.*

Another object of the invention is the application of these primers for the detection and the numeration of *C. perfringens.*

DESCRIPTION OF THE PRIOR ART

*Clostridium perfringens* type A is widely distributed (soil, sewage, intestinal tracts of humans and animals), and is a common causative agent of bacterial food poisoning outbreaks worldwide. The symptoms, predominantly diarrhea and abdominal pain, appear 6 to 24 hours after ingestion of contaminated food. Vomiting and fever are unusual. Death occurs occasionally among debilitated persons, particularly the elderly.

*C. perfringens* enterotoxin CPE which is produced during the sporulation phase has been shown to produce the symptoms associated with *C. perfringens* food poisoning. The illness is caused by the ingestion of food that contains larger number of vegetative enterotoxigenic *C. perfringens* (more than $10^5$ organisms per g). These bacteriae multiply and sporulate, releasing CPE into the intestine.

A *C. perfringens* count of more than $10^6$/g in fecal samples of ill persons is indicative of *C. perfringens* food poisoning. In addition, CPE detection directly in fecal samples is a valuable method confirming the diagnosis.

The epidemiological investigations involve *C. perfringens* numeration in suspected foods. The characterization of the enterotoxigenic *C. perfringens* strains is not used routinely, since *C. perfringens* sporulates poorly in usual culture media.

Recently, CPE and phospholipase C gene sequences have been determined (VAN DAMME et al. 1989, Ant. Van Leeuwen 56, 181–190; TSO J. and SIEBEL, 1989. Infect. Immun. 57: 468–476, TITBALL et al. 1989 Infect. Immun. 57:367–376). The phospholipase C gene is located on a variable region of the chromosomal DNA in all *C. perfringens* toxinotypes whereas the distribution of CPE gene is restricted. Only 6% of the *C. perfringens* isolates from various origins showed the presence of CPE gene by DNA—DNA hybridization. This ratio is higher (59%) among *C. perfringens* strains isolated from confirmed outbreaks of food poisoning. In the standard methods the enterotoxin detection by biological or immunological tests requires previously the sporulation of *C. perfringens*. Several specific medium and protocols for *C. perfringens* sporulation have been described, but they are time consuming and many *C. perfringens* strains do not sporulate or very poorly (DUCAN and STRONG, 1968. Appl. Microbiol. 16: 82; PHILIPS, 1986, Lett. Appl. Microbiol 3: 77–79), which impairs the CPE detection.

A method for the detection of *C. perfringens* by polymerase chain reaction (PCR) has yet been disclosed during the third Congress of the French Society of Microbiology (Apr. 21–24, 1992) through a poster of FACH et al.

The method consisting of an amplification of the parts of the genes encoding the α-toxin, also called lecithinase, and the enterotoxin of *C. perfringens* by using oligonucleotidic primers which were choosen in these genes. However, the sequence of the primers used for carrying out this method was not disclosed and the sensitivity mentioned by the authors was low, i.e. from 500 to 5000 bacteriae per gram of feces.

Moreover, the results were obtained on feces artificially contaminated and not on feces from contaminated patients or on contaminated food.

The inventors have thus sought to elaborate a sensitive and reliable method allowing the detection of low quantities of bacteriae in samples of different origins, such as in feces or food, in a raw form.

They have surprisingly shown that it is necessary to choose the primers in some well determined regions of the genes, as well as in the gene of the enterotoxin that is one of the lecithinase.

Besides, they have carried out a process for the treatment of foods samples, allowing a specific, sensitive and reliable determination of the presence of the *C. perfringens* contained in these foods.

SUMMARY OF THE INVENTION

The present invention firstly relates to primers for the amplification of the gene encoding the lecithinase of *C. perfringens*, also called alphatoxin or phospholipase C, corresponding to a part of the sequence of the gene comprised between the nucleotides 1350 and 1850, and preferentially between nucleotides 1350 and 1470 or 1650 and 1850, and which can amplify at least a part of the said gene, by cooperating with other primers having similar features and having a reversed polarity.

The said primers comprise prefentially from 10 to 40 and more preferentially from 10 to 30 nucleotides and their sequences can be one of the following ones:

SEQ ID NO:1 (PL3) AAG TTA CCT TTG CTG CAT AAT CCC

SEQ ID NO:2 (PL7) ATA GAT ACT CCA TAT CAT CCT GCT

SEQ ID NO:3 (Plc) TCA AAA GAA TAT GCA AGA GGT

SEQ ID NO:4 (PL1) TTCTAT CTT GGA GAGG CTATG-CAC

SEQ ID NO:5 (PL4) GCTACTAGTTCTTTTACAT-TCTTTCC.

The invention relates besides to primers for the amplification of the gene encoding enterotoxin of *C. perfringens,* corresponding to a part of the sequence of the gene comprised between the nucleotides 450 and 950 and preferentially between the nucleotides 450 and 550, or the nucleotides 750 and 950 of said gene, and which can amplify at least a part of the said gene, by cooperating with other primers having similar features and having a reversed polarity.

The said primers comprised prefentially from 10 to 40 and more preferentially from 10 to 30 nucleotides and their sequences can be one of the following ones:

SEQ ID NO:6 (P145) GAA AGA TCT GTA TCT ACA ACT GCT GGT CC

SEQ ID NO:7 (P146) GCT GGC TAA GAT TCT ATA TTT TTG TCC AGT

SEQ ID NO:8 (Ent A) GAA CGC CAA TCA TAT AAA TTT CCA GCT GGG

The present invention relates moreover to a process for the determination of the presence of the gene encoding the lecithinase, or of the gene encoding the enterotoxin, in a sample, comprising the following steps:

the DNA from the sample is isolated, parts of the genes encoding the lecithinase, or the enterotoxin, are amplified by polymerization chain reaction (PCR) with the help of specific primers, such as defined hereabove respectively for the lecithinase and for the enterotoxin, the amplification products are determined with the help of known methods.

The present invention is further directed to a new *C. Perfringens* beta toxin gene, called $\beta_2$ gene, as hereinbelow described.

Another object of the present invention is a process for the determination of the presence, and the numeration of *C. perfringens* in a sample, wherein:

the DNA from the said sample is isolated, parts of the genes encoding the lecithinase and the enterotoxin are amplified by polymerase chain reaction with the help of specific primers such as defined hereabove for respectively the lecithinase and the enterotoxin, the amplification products are determined with the help of known methods.

The amplification products obtained by the process described hereabove can in particular be determined by electrophoresis on an agarose gel, followed by a transfer of the eluted DNA on "Nylon" membranes and by an hybridation with a labelled probe specific for the amplified part of the gene.

Other methods known by the man skilled in the art can also be used, if such methods are sufficiently specific and sensitive.

Such methods are in particular described in "The molecular cloning: A Laboratory Manual; SANDERS et al., Cold Spring Harbor Editor", in which the man skilled in the art can refer for carrying out the processes according to the present invention.

The choice of the hereabove described primers did not obviously emerge from the genes sequences such as published. Indeed, the man skilled in the art well knows that the choice of primers for the amplification of a given DNA part is difficult and that one can be faced with numerous difficulties.

For example, primers can lack of specificity or be weakly thermodynamicly stable.

The man skilled in the art can also be faced with other technical difficulties from different types. Thus, the choice that has to be made by the man skilled in the art in the sequence of the gene is difficult because of the important number of thinkable combinations between the two primers corresponding respectively to sequences of the two strands, from the DNA molecule which has to be amplified.

The use of softwares help the man skilled in the art in his choice but does not constitue a method leading automatically and obviously to primers permitting the sought amplification.

The primers such as defined hereabove are able to amplify the said genes if they cooperate with another primer having similar features but of reversed polarity. Indeed, the other primer must be situated on the strand of reversed polarity, called non-sense strand, in such a way that the polymerization of the two strands, initiated from the two primers produce two types of single strand DNA fragments which hybridate and form a double strand DNA molecule, called amplification product, which will be determined by known methods. The primer cooperating in the amplification of the fragment of the said gene have some similar features, i.e. that it is situated in the region of the said gene but on the strand of reversed polarity.

Preferentially, the combinations of the primers can be the following: PL1 and PL4, PL3 and PL7, P145 and P146, P145 and Ent A.

The processes hereabove described allow the detection of *C. perfringens* in a lot of samples, such as feces or food products, such as convenients foods, without necessiting a pretreatment of the sample.

In a general way, heating of the samples at temperature lysing the bacteriae and separating by centrifugation the DNA from bacterial fragments is sufficient.

In the case of food samples, in particular meats, it can be necessary to perform a pretreatment of the sample in order to eliminate substances which can interfer with the polymerase chain reaction.

Thus, the DNA can be isolated from a food sample by a process comprising the following steps:

the sample is incubated in a medium allowing the growth of *C. perfringens,* the bacteriae are separated from the food particles by centrifugation, the bacteriae are put in contact with a resin which lyses them, the DNA is separated from bacterial fragments.

The present invention also relates to a new *C. perfringens* beta toxine gene which has been identified, isolated and characterized.

Said gene, called $\beta_2$ gene, can be isolated from the *C. Perfringens* strains of C-type. Two corresponding plasmids were filed on Dec. 12, 1994 at the CNCM Collection of Institut Pasteur and were registered respectively under the reference I-1499 for TGI/pMRP 109 and under the reference I-1500 for TGI/pMRP 126.

SEQ ID NO 9 pMRP109

```
1    AAA GAA ATG GAT GCG TAT AGG AAA GTG ATG GAG AAT TAT CTT AAT GCT   48
1     K   E   M   D   A   Y   R   K   V   M   E   N   Y   L   N   A    16

49   TTA AAA AAC TAC GAT ATT AAT ACA GTT GTA AAC ATT TCA GAA GAT GAA   96
17    L   K   N   Y   D   I   N   T   V   V   N   I   S   E   D   E    32

97   AGA GTA AAT AAT GTT GAA CAG TAT AGA GAA ATG TTA GAA GAT TTT AAA  144
33    R   V   N   N   V   E   Q   Y   R   E   M   L   E   D   F   K    48

145  TAT GAT CCT AAC CAA CAA CTG AAA TCT TTT GAA ATA CTT AAT TCA CAA  192
49    Y   D   P   N   Q   Q   L   K   S   F   E   I   L   N   S   Q    64

193  AAG AGC GAT AAT AAA GAA ATA TTT AAT GTA AAA ACT GAA TTT TTA AAT  240
65    K   S   D   N   K   E   I   F   N   V   K   T   E   F   L   N    80
```

-continued

```
241 GGT GCA ATT TAT GAT ATG GAA TTT ACT GTA TCA TCT AAA GAT GGA AAA 288
81   G   A   I   Y   D   M   E   F   T   V   S   S   K   D   G   K  96

289 TTA ATA GTA TCT GAT ATG GAA AGA ACA AAA GTT GAG AAT GAA GGA AAA 336
97   L   I   V   S   D   M   E   R   T   K   V   E   N   E   G   K  112

337 TAT ATT TTA ACA CCA TCA TTT AGA ACT CAA GTT TGT ACA TGG GAT GAT 384
113  Y   I   L   T   P   S   F   R   T   Q   V   C   T   W   D   D  128

385 GAA CTA GCA CAA GCA ATT GGG GGA GTT TAT CCA CAA ACA TAT TCT GAT 432
129  E   L   A   Q   A   I   G   G   V   Y   P   Q   T   Y   S   D  144

433 AGA TTT ACA TAT TAT GCA GAT AAT ATA TTA TTA AAC TTC AGA CAA TAT 480
145  R   F   T   Y   Y   A   D   N   I   L   L   N   F   R   Q   Y  160

481 GCA ACT TCA GGT TCA AGA GAT TTA AAA GTA GAA TAT AGT GTT GTA GAT 528
161  A   T   S   G   S   R   D   L   K   V   E   Y   S   V   V   D  176

529 CAT TGG ATG TGG AAA GAT GAT GTT AAA GCT TCT CAA ATG GTA TAT GGT 576
177  H   W   M   W   K   D   D   V   K   A   S   Q   M   V   Y   G  192

577 CAA AAT CCT GAT TCT GCT AGA CAA ATA AGA TTA TAT ATA GAA AAA GGA 624
193  Q   N   P   D   S   A   R   Q   I   R   L   Y   I   E   K   G  208

625 CAA TCT TTC TAT AAA TAT AGA ATA AGA ATT AAA AAC TTT ACA CCT GCA 672
209  Q   S   F   Y   K   Y   R   I   R   I   K   N   F   T   P   A  224

673 TCA AT
225  S
```

pMRP109 is a recombinant plasmid containing the beginning of the beta toxin 2 gene.

pMRP109 was produced by insertion into the pUC19 vector restricted by SmaI of a DNA fragment amplified by PCR from the total DNA of strain CWC 245 of *C. perfringens* type C and primers deduced from the N-terminal protein sequence of beta 2 (P279) and an internal protein sequence (P280):

SEQ. ID NO:10 P279 5'-AAA GAA ATI GAT GCI TAT AGI AAA GTI ATG G-5'

SEQ. ID NO:11 P280 5'-AT IGA IGC IGG IGT AAA ATT-3'.

The complete DNA inserted into pMRP109 was sequenced. This DNA corresponds to the beginning of the beta toxin 2 gene and codes for the first 225 amino acids of the functional protein.

SEQ. ID NO:12 pMRP126 pMRP126 is a recombinant plasmid containing the end of the beta 2 gene.

pMRP126 was produced by cloning a DNA fragment of about 400 base pairs cleaved by Sau3A from *C. perfringens* type C strain CWC245 in the pUC19 vector cleaved by BamHI.

This part of the beta 2 gene codes for amino acids 176 to 236. Nucleotides 526 to 677 are common with the last 151 nucleotides of pMRP109.

BRIEF DESCRIPTION OF THE DRAWINGS

FIG. 2 is the microsequencing of purified beta toxin from strain CWE 245.

```
                                                            GAT 528
                                                             D  176

529 CAT TGG ATG TGG AAA GAT GAT GTT AAA GCT TCT CAA ATG GTA TAT GGT 576
177  H   W   M   W   K   D   D   V   K   A   S   Q   M   V   Y   G  192

577 CAA AAT CCT GAT TCT GCT AGA CAA ATA AGA TTA TAT ATA GAA AAA GGA 624
193  Q   N   P   D   S   A   R   Q   I   R   L   Y   I   E   K   G  208

625 CAA TCT TTC TAT AAA TAT AGA ATA AGA ATT AAA AAC TTT ACA CCT GCA 672
209  Q   S   F   Y   K   Y   R   I   R   I   K   N   F   T   P   A  224

673 TCA ATT AGA GTA TTT GGT GAA GGG TAT TGT GCA TAG AAA AAA ATA TGA 720
225  S   I   R   V   F   G   E   G   Y   C   A   *                  236

721 AGT GAC TTA GTC ACT TCA TAT TTT TTT TAC TAT TAA TTT TAT TAT ATA 768

769 AAA ACC TAA CAT ACA TGA AAG TAT TCT TAA TAC AGT TAT ATC AAA ATT 816

817 AAA GTA GGG GAA ATA AAA TAA AAG GCT AAA AAC TAT ATT AAA AAC TAT 864

865 AAA AAT TAT TAA ATT AGG                                         882
```

FIG. 3 is the partial nucleotide sequence and translation into amino acids of beta 2.

FIG. 4 is a comparison of amino acid sequences of beta 2 and beta 1 toxin using the GCG Gap program.

Figure 1A:
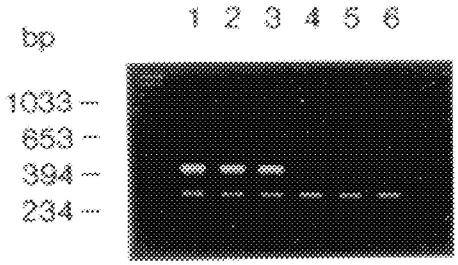
FIGS. 1A, 1B and 1C are ethidium bromide stained agarose gel of amplification products with different strains of enterotoxigenic *C. perfringens.*
Figure 1B:
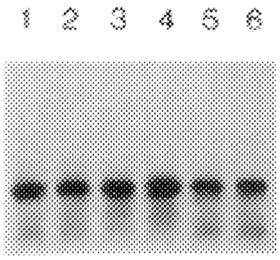
Figure 1C:
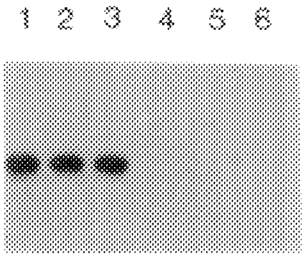

The present invention is illustrated without being limited by the following examples in which FIG. 1 is an ethidium bromide stained agarose gel of amplification products obtained with enterotoxigenic *C. perfringens* type A strain 8-6 (1), type D strain IP76 (2), type E strain NCIB10748 (3), and non enterotoxigenic *C. perfringens* type A strain ATCC13124 (4), type B strain CN3922 (5) and type C strain CWC236 (6) (Panel A), and Southern hybridization with Plc (Panel B), and EntA (Panel C) probes.

MATERIALS AND METHODS

Bacterial strains

All bacterial strains used in this study are listed in table 1. The others *C. perfringens* strains were isolated from food poisoning outbreaks and feces of children suffering from diarrhoea (see table 1).

Clostridium were grown, under anaerobic conditions, in TYG medium: trypticase (30 g/l), yeast extract (20 g/l), glucose (5 g/l) and cysteine HCl (0.5 g/l), pH 7,2. Strains were confirmed as *C. perfringens* by lactose fermentation, nitrate reduction, gelatinase production and absence of motility.

Standard bacteriological methods

For bacteriological food and feces analysis, 10 g of the samplee were weighted aseptically into sterile stomacher bags and homogenized for 2 minutes with 90 ml of peptoned water. One ml of decimal dilutions of the suspension was mixed with 9 ml SPS agar: Tryptone (15 g/l), yeast extract (10 g/l), feric citrate (0.5 g/l), sodium sulfite (0.5 g/l), sodium thioglycolate (0.1 g/l), tween 80 (0.005 g/l), polymyxine B sulfate (0.001 g/l), disodic sulfadiazine (0.12 g/l) and agar (14 g/l pH 7). After a 18 h anaerobic incubation at 46° C. the number of sulfito-reductor Clostridium was determined. Colonies surrounded with the black characteristic precipitate were identified by biochemical test (lactose fermentation, nitrate reduction, gelatinase production and motility).

Anti *C. perfringens* enterotoxin immunoglobulins

*C. perfringens* enterotoxin was purified from *C. perfringens* strain 8-6 and rabbit anti *C. perfringens* enterotoxin antibodies were prepared as previously described (POPOFF, 1984, FEMS MICROBIOL Let.21: 1–5). Anti *C. perfringens* enterotoxin immunoglobulins were purified by immunoaffinity. *C. perfringens* enterotoxin (3–5 mg) was coupled to 1 g of cyanogen bromide—activated Sepharose 4B (Pharmacia, Paris, France) according to the instructions of the manufacturer. Five ml of rabbit anti *C. perfringens* enterotoxin serum were passed over the immuno affinity column. The column was washed with phosphate-buffered saline (PBS) until no protein was detected, and eluted with 1M acetic acid. Fractions of 200 $\mu$l were collected into tubes containing 100 $\mu$l TRIS 3M pH 8. The fractions containing anti *C. perfringens* enterotoxin immunoglobulins were dialyzed against PBS.

Preparation of latex beads

Coating of latex beads (Bacto Latex 0.81, Difco, USA) was performed as described (SHAHRABADI et al. 1984, Clin. Microbiol. 20: 339–341). Latex suspension (2–5 ml) was diluted in 15 ml of glycine buffer (0.1M glycine, 0.15M NaCl, pH 8.2) containing 200 $\mu$g of specific anti *C. perfringens* enterotoxin immunoglobulins, and homogenized for 1 minute at room temperature. Then, 1 volume of PBS—0.1% bovine serum albumine (BSA) was added. The mixture was shaken by vortex mixing, and stored at 4° C. The negative latex control was prepared as the same, but using non immune IgG (Sigma, Paris, France).

Slide latex agglutination test (SLAT) for *C. perfringens* enterotoxin detection.

SLAT was performed on a glass slide by mixing 25 $\mu$l of coated latex and 25 $\mu$l of serial ten fold dilutions of samples in PBS—0,5% BSA.

The mixture was gently rotated and the results were recorded after 3 minutes.

The enterotoxin detection in *C. perfringens* strains was carried out using SLAT and culture supernatant from cultures in the Duncan and Strong sporulation medium (DAMME-JONGSTEN et al. J. Clin. Microbiol. 28: 131–133).

Fecal specimens were diluted at 1:10 in PBS—0.5% BSA, homogenized by vortexing, and centrifuged at 15 000×g for 30 minutes. The clarified supernatant was tested by SLAT.

Primers used in duplex PCR

The oligonucleotides for PCR amplification and for hybridization used in this study, the primers PL3, PL7, PL1, PL4 and Plc were derived from the *C. perfringens* alphatoxin gene (11), the primers P145 and P146 and the probe Ent A were from the enterotoxin gene (VAN DAMME et al. 1989, cited above).

All the oligonucleotides were chemically synthesized by using a nucleic acid synthesizer (model 380 B; Applied Biosystems Inc. Foster City, Calif.).

Duplex PCR with broth culture

One ml of overnight bacterial cultures were transferred to a microcentrifuge tube and centrifuged at 12.000×g for 3 minutes. The pellet was resuspended in 100 $\mu$l water, heated at 100° C. for 10 minutes, and centrifugated at 12000×g for 10 minutes. Five $\mu$l of the supernatant were submitted to PCR using a PTC-100 programmable Thermal Controller (M.J. Research Inc. Watertown, Mass., USA). Each reaction tube contained 50 $\mu$l of a solution of 10 mM Tris-HCl pH 8.3, 50 mM KCl, 1.5 mM $MgCl_2$, 0.1 mg/ml gelatine, 200 $\mu$M of each of the deoxynucleotide (Boehringer Mannheim, Germany), 0.5 $\mu$M of each primer and DNA sample. Evaporation within the tube was prevented by the addition of 100 $\mu$l mineral oil (Sigma, St-Louis, Mont., USA). The reaction mixtures were treated to 94° C. for 5 minutes to denature the DNA and then 2.5 units of Taq polymerase (Boehringer) were added to each tube. All PCR reaction were performed using 45 cycles of the optimized thermal profile: 30 s denaturation at 94° C., 30 s primer-annealing at 55° C. and 30 s primer-extension at 72° C. After the 45th cycle, the extension reaction was continued for another 10 minutes at 72° C., to ensure that the final extension steps was complete. Negative controls containing all reagents except template DNA were performed in each amplification set. To avoid contamination, sample preparation, PCR amplification and electrophoresis were performed in three different rooms.

Duplex PCR with stool samples

Stool samples (0,1 g) were weighed aseptically into sterile tubes and homogenized with 0,9 ml of water. Samples were centrifugated at 12.000×g for 3 minutes. The pellet was resuspended in 100 $\mu$l water, heated at 100° C. for 10 minutes, centrifugated at 12000×g for 10 minutes, and 5 $\mu$l of the supernatant were PCR amplified as described above.

Pretreatment of food samples before the amplification reaction a) Incubation of the sample The detection of viable bacteriae is of great importance in the food processes.

The discrimination between dead and alived bacteriae can be performed by cultivating the sample.

For the detection of *C. perfringens,* 25 g of the sample are incubated in 225 ml of buffered peptonized water for 18 hours at 37° C. in anaerobiosis and without shaking.

The spores of *C. perfringens* are selected with the help of a thermal shock at 80° C. of the food culture before incubating.

b) Treatment of the sample for the PCR analysis

After incubation of the food cultures, the food fragments are sedimentated and 1 ml of the enrichment medium is taken at the surface.

A low speed centrifugation (600 rpm) allows the elimination of the lowest food particles. The supernatent is recovered and centrifugated at a high speed (12 000 rpm) for 2 minutes. The supernatant is eliminated and the bacterial pellet is suspended in 2 ml of sterile water. The tube is then centrifuged at 12 000 rpm and the supernatant is eliminated with the help of a Pasteur pipette.

200 $\mu$l of the "InstaGene" matrix (commercialized by Biorad) are added on the pellet and incubated at 56° C. for 30 minutes. The tube is vortexed during 10 seconds and put in a water bath at 100° C. during 8 minutes. The tube is then vortexed for 10 seconds and centrifuged at 12 000 rpm for 3 minutes. 3 $\mu$l of the supernatant are taken in order to perform the duplex PCR which is finally performed on a volume of 50 $\mu$l.

Starting from 25 g of foods containing 10 or more than 10 *C. perfringens* allows the determination in the 15 $\mu$l of the amplified solution of the amplification product.

Gel Electrophoresis

A 10 $\mu$l aliquot of amplified DNA was examined after electrophoresis through a composite agarose gel consisting of 3% NuSieve agarose and 1% SeaKem agarose (FMC BioProducts, Ropckland, (Me., USA) and containing 0.5 $\mu$g/ml ethidium bromide, in 1× Tris-borate-EDTA buffer (0.089M Tris, 0.089M bioric acid, 0.002M EDTA, pH 8). Electrophoresis was carried out for 1 hour a t 80 V. The gel was examined visually with an ultra-violet transilluminator.

Hybridization procedure

DNAs electrophoresed on agarose gel were transferred to "Nylon" membranes (Boehringer, Paris, France) using 0.4N NaOH and fixed by heating the membranes for 15 minutes at 120° C. Filters were pre-hybridized in 5× Saline Sodium Citrate buffer (SSC), 0.1% N-laurylsarcosine, 0.02% Sodium Dodecyl Sulfate (SDS) in 1% blocking reagent (Boehringer) at 65° C. for 1 hour. Hybridization occurred with Ent A or Plc oligonucleotide 3'-endlabelled by digoxigenin 11-DUTP with terminal deoxynucleotidyl-transferase (Boehringer). The probe was added to 50 ng/ml in the pre-hybridization solution and filters were incubated at 40° C. for 1 hour. After 2× SSC, 0.1% SDS washing, membranes were washed to a final stringency of 50° C. in 0.1× SSC, 0.1% SDS and detection was performed with alkaline phosphatase-labelled anti-digoxigenin antibody (Boehringer), nitroblue tetrayolium (NBT) and bromo-4-chloro-3-indolyl phosphate (BCIP) according to the instruction of the manufacturer (Boehringer).

EXAMPLE 1

*C. perfringens* duplex PCR specificity and characterization of the enterotoxigenic strains The specificity of the duplex PCR with the two primers sets derived from the phospholipase C and CPE genes was assessed by using different Clostridium species and various bacterial species frequently encountered in foods (table 1). The 283 bp amplification product was observed in ethidium bromide stained agarose gel with all *C. perfringens* strains tested (table 1). This amplification product had the expected size of the phospholipase C gene DNA fragment generated by PL3 and PL7 primers set. This result was confirmed by DNA—DNA hybridation with the internal primer Plc (FIG. 1).

The other bacterial strains tested showed no amplification products with the two primers sets PL3–PL7 and P145–P146 (table 1).

Seven *C. perfringens* strains out of 24 showed an additional 426 bp amplification product which corresponded to the expected size of the CPE DNA fragment delimited with P145 and P146. This 426 bp amplification product hybridized with the Ent A primer localized between P145 and P146 on the CPE DNA sequence and not with Plc primer derived from the phospholipase C gene (FIG. 1).

The *C. perfringens* strain 8.6 was found enterotoxinogenic by the duplex PCR amplification (table 1). This data is in agreement with the fact that this strain produced CPE using Vero cell cytotoxicity, mouse lethality and immunoprecipitation.

EXAMPLE 2

Sensitivity of the duplex PCR using broth cultures

The duplex PCR was performed directly with broth cultures of the enterotoxogenic *C. perfringens* strain 8.6, in order to determine the sensitivity of the method. The number of bacteriae in culture samples was determined microscopically using a Petrov Chamber. The PCR amplification was carried out as described in material and methods. It was found that as few as 50 bacteria in the reaction volume yielded positive results after agarose gel electrophoresis and ethidium bromide staining. The sensitivity was 10 fold increased when the amplification products electrophoresed on agarose gel were transferred to nylon membrane and hybridized with digoxigenin labelled internal probes Ent A and Plc. In these condituions, the detection limit was approximately 5 bacteria in the reaction volume of the duplex PCR.

EXAMPLE 3

Application of the duplex PCR to stool samples

Twenty three stool samples originated from a suspected *C. perfringens* food borne intoxication outbreak were investigated directly by the duplex PCR and standard microbiological methods for *C. perfringens* detection. Eighteen samples were found positive in the duplex PCR (table 2). All these samples yielded two amplifications products which has the expected size of the DNA fragments delimited by PL3–PL7 and P145–P146, and hybridized with the internal primers Plc and Ent A respectively, signifying that they contained enterotoxigenic *C. perfringens.* The sulfito reductor bacteria counted by the standard bacteriological methods ranged from less than $10^4$ to $10^8$ bacteria per gram. Five feces samples were found negative in the duplex PCR and DNA—DNA hybridization test. The corresponding sulfito-reductor bacteria counting was less than $10^4$ per gram for 3 samples, and $10^5$ to $2.10^5$ for the two other (table 2).

EXAMPLE 4

*C. perfringens* enterotoxin SLAT in stool samples

The CPE was detected in 18 stool samples out of 23 by SLAT as described in material and methods (table 2). Enterotoxigenic *C. perfringens* was identified by the duplex PCR in 17 of these 18 SLAT positive stool samples. Four samples were negative with both tests.

One stool sample was shown to contain enterotoxigenic *C. perfringens* by the duplex PCR and no CPE by SLAT. The low number of enterotoxigenic *C. perfringens* (less than $10^4$ per gram) explained the absence of CPE in this example.

CPE was detected by SLAT in one stool sample (table 2) which was negative in the duplex PCR. The level of sulfito reductor bacteria in this sample was $10^5$ per gram. However, twenty *C. perfringens* clones isolated on sheep blood agar, were identified as enterotoxigenic *C. perfringens* by the duplex PCR.

EXAMPLE 5

Application of the duplex PCR to naturally and artificially contaminated food samples The food sample which was responsible of the food intoxication outbreak was found to contain enterotoxigenic *C. perfringens* by the duplex PCR performed directly without enrichment culture. The counting of sulfitoreductor bacteria was $10^5$ per g, and no CPE was detected by SLAT.

In order to investigate the sensitivity of this method, the duplex PCR was assayed directly with artificially contaminated food samples. The detection limit was found to be $10^5$ *C. perfringens* per g. The sensitivity was improved by using an overnight enrichment culture as described in material and methods. Among 59 naturally contaminated food samples, 2 were found to contain $5.10^5$ and $10^3$ *C. perfringens* per g respectively by the classical method and were positive by the duplex PCR.

All the 57 food samples which did not contain sulfitoreductor bacteria and were artificially contaminated (10 *C. perfringens* per g) gave a positive result in duplex PCR after enrichment culture (table 3).

CONCLUSION

All the 24 *C. perfringens* strains tested yielded the 426 bp DNA fragment hybridizing with the probe Plc, which corresponds to the presence of the phospholipase C gene. Seven of these *C. perfringens* strains (2 type A reference strains, 3 type A strains isolated from food, and 2 type D strains) showed an additional amplification product hybridizing with Ent A probe, which indicates the presence of the CPE gene.

The duplex PCR is specific of *C. perfringens.* No amplification product was observed with 27 Clostridium strains different from *C. perfringens* and 20 other bacteria species frequently encounted in foods.

An important advantage of this method is to identify easily and quickly the enterotoxigenic *C. perfringens* strains.

The duplex PCR can be used with *C. perfringens* grown in regular culture medium for anaerobic bacteria without DNA purification. The sensitivity of the duplex PCR using pure culture is 50 bacteria by visualization of ethidium bromide stained amplification product in agarose gel, and 5 bacteria in the reaction volume by DNA—DNA hybridization with the internal probes.

This duplex PCR DNA—DNA hybridization assay was tested with biological and food samples. Enterotoxigenic *C. perfringens* were detected directly in 18 among 23 stools samples from patients suffering food borne intoxication. These results were in agreement with the numeration of the sulfito reductor bacteria by the standard method and the detection of the CPE by SLAT, except for two stools samples. One stool sample containing $10^5$ sulfito reductor bacteria per gram and CPE by SLAT was found negative by the duplex PCR. But, individual *C. perfringens* clones isolated from this stool sample were identified as enterotoxigenic *C. perfringens* by the duplex PCR. The presence of PCR inhibitors in this sample accounts probably for this negative result. The other stool sample showed a low number of sulfito-reductor bacteria and no detectable CPE, but was positive in the duplex PCR. A contamination of this sample could explain the positive result in duplex PCR.

The detection limit of enterotoxigenic *C. perfringens* in stools by the duplex PCR is $10^4$ and $10^5$ per gram. This sensitivity is suitable for the diagnosis of *C. perfringens* food borne intoxication, since it has been reported that *C. perfringens* is recovered at high number ($10^6$ and more per g) in stools from patients suffering *C. perfringens* food borne intoxication.

Controls of food *C. perfringens* contamination constitute an important step in the prevention of food born intoxication by this microorganism. The standard method routinely used detects sulfito-reductor bacteria which encompasse *C. perfringens* and also other Clostridium. The duplex PCR is specific of *C. perfringens* and discriminates the enterotoxigenic strains which are the causative agents of *C. perfringens* food borne intoxication. The sensitivity of this method (10 *C. perfringens* per g) performed with enrichment cultures of food samples is compatible with the prescribed detection levels for food controls. The limit of the duplex PCR directly with food samples without enrichment cultures is $10^5$ bacteria per g, the duplex PCR can be used directly when a *C. perfringens* food borne intoxication is suspected.

The duplex PCR is more rapid and simple than the standard procedure which needs additional bacteriological tests for the identification of the suspected clones. This method can be applied to food controls for the detection of *C. perfringens* and identification of the enterotoxigenic strains.

EXAMPLE 6

Further experiments illustrating the application of the duplex PCR according to the invention to the detection of *C. perfringens* in foodstuffs, are presented hereinbelow.

1) Animal Feed

Several samples of animal feed have been analyzed for the presence of *C. perfringens.* These feeds were made up of meat, fish or bone meals. The concentration of sulfito-reductor anaerobic organisms cultivated at 46° C. have been determined in 44 naturally contaminated foods and more precisely the presence of *C. perfringens* spores has been ascertained by use of LS medium (BEERENS H, Romond Ch., Lepage C., Criquelion J. (1982). A liquid medium for the enumeration *Clostridium perfringens* in food and faeces. In "Isolation and identification methods for foods poisons organisms", pp. 137–149. Ed. Corry J. E. L., Roberts D. and Skinner F. A. Academic Press London) and by the PCT duplex technique described previously. Spore selection was carried out by thermal shock treatment at 80° C. for 10 minutes. The presence of inhibitors for the gene amplification reaction (PCR) led to use an extraction and purification procedure for the nucleic acids which involved the "Insta Gen" (Bio-Rad) matrix and which has been described previously.

On the 44 samples analyzed (table 4) 12 were positive according to the procedure using the LS medium and the PCR duplex test. 24 samples were negative with both methods. 36 samples out of the 44 analyzed gave the same results for the two methods, giving a correlation rate of over 80% between the bacteriological method and the genetic test. For 5 samples the PCR duplex method seemed to be more sensitive than the procedure using the LS medium. For these 5 samples it was possible to isolate, from the thioglycolate liquor incubated for 48 hours, at least one colony on TSC medium which had the biochemical characteristics of *C. perfringens.* The low concentration of *C. perfringens* (<10/g) in the samples was only detected by the PCR technique, which was more sensitive than the procedure using thee LS medium.

Three samples were found to be positive with the procedure using LS medium but stayed negative with the PCR duplex test. These samples contained respectively 7.2 and 1 ASR per gram. In order to ascertain whether the PCR duplex test had not been compromised by the presence of inhibitors remaining after the nucleic acid extraction phase, a few nanograms of *C. perfringens* DNA (2 ng) were added to the extracts obtained from the 3 samples and the gene amplification test was again carried out under the same conditions. The 3 tests then became positive showing that no inhibitor effect had been observed initially. In addition, the 10 ASR colonies corresponding to these 3 samples were subjected to biochemical identification and a PCR duplex test. These 2 analyses still remained negative, showing evidence of the absence of *C. perfringens* in these samples. In fact, bearing in mind the difficulties in interpretation of the method described by BEERENS and al. (the presence of gas in ⅓ of the Durham belljar and the presence of a black precipitate at the bottom of the tube were sometimes evaluated differently according to the users) and the very doubtful results obtained for these 3 samples, it seems that these 3 samples correspond to false positives in the method described by BEERENS and al.

2) Human Foodstuffs

Within the framework of systematic monitoring of food hygiene, the number of *C. perfringens* which can be identified is generally low ($<10^2$ per gram). Various foods (cooked dishes, beef, cooked meats, fish, powdered milk) were analyzed using the PCR duplex technique and the results were compared with those obtained by the standard bacteriological method (standard method ISO 7937).

Only 3 samples were found to be positive according to the two methods, the other 27 containing no *C. perfringens.* The PCR test allowed the detection of *C. perfringens* in 24 hours, while the bacteriological method was much longer (48–72 h). The foods concerned were packs of a frozen ground beef and potato dish. They were contaminated by type A non-enterotoxinogenic *C. perfringens.*

EXAMPLE 7

Study of the *C. Perfringens* Beta Toxin Gene

In order to apply a PCR type method to the identification of type C *C. perfringens* strains responsible for necrotic enteritis, it was necessary to determine the sequence of the beta toxin gene.

The applicant carried out the production and purification of the beta toxin from the CWC 245 strain of *C. perfringens*, then determined peptide sequences, produced oligonucleotide markers and finally carried out the cloning and sequencing of this gene.

(1)—Production and purification of the beta toxin

Cultures were made on TGY (Trypticase 30 g/l, yeast extract 20 g/l, glucose 25 g/l, pH 7.5) in a 2 1 fermenter with continuous nitrogen flow, moderate stirring and regulation of pH at 7.5.

After 5 hours at 37° C., cholesterol in alcoholic solution (20 mg/l) was added to the culture in order to precipitate the theta toxin. The culture was centrifuged at 10 000 g at 4° C. for 20 minutes. The supernatant was precipitated by 60% saturated ammonium sulfate. After centrifuging at 20 000 for 20 minutes, the residue was dissolved in PBS (pH 6.8) and reduced with 50 mM of dithiothreitol. The sample was added in 3 fractions to a biogel P4 (Bio-rad) column equilibrated in PBS. The eluted proteins were applied to a column of thiopropyl-Sysharon 6B (58 g of resin expanded in PBS) and a flow of 5 ml/h. The column was washed with 100 ml of PBS. Under these conditions the beta and delta toxins were not retained on the column, while the theta and alpha toxins were retained. The effluent was concentrated by ultrafiltration on a PM 10 (Millipore) membrane and submitted to preparative iso-electrofocalization (16 000 V for 16 hours) with a pH gradient of 3.5 to 8. The material focalized between pH 5.3 and 5.5 was collected and concentrated by ultrafiltration.

The concentrated fraction was added to a column of Biogel P100 (Biorad) equilibrated in PBS and the different fractions were tested by electrophoresis in polyacrylamide-SDS gel. In this way the beta toxin was purified to homogeneity (MW 28 000 and pH 5.4–5.5).

The purified beta toxin was lethal to mice (4 μg, IV), dermonecrotic after injection into guinea-pig skin (2 μg), and enteronecrotic after injection into rabbit intestinal loop (40 μg). The enterotoxic effect was inhibited by incubation of the beta toxin with trypsin.

(2) Protein microsequencing of the beta toxin and oligonucleotides

The purified beta toxin was electrophoresed on polyacrylamide-SDS, then transferred onto Immobilon membrane and subjected to microsequencing of the N-terminal region.

The internal protein sequences were obtained by tryptic digestion of the beta toxin, purification of the different peptides by HPLC chromatography and microsequencing of peptides 21, 23 and 13.

Oligonucleotides deduced from the protein sequences were synthesized taking into account of the normal codon of Clostridium and with inosines (I) in the most degenerate positions (FIG. 2).

(3) Hybridization of the oligonucleotides

The synthetized oligonucleotides were tested for hybridization with total DNA of CWC 245 digested by different restriction enzymes. The hybridizations were carried out over 16 hours at 40° C. with oligonucleotides labeled with $^{22}P$ by polynucleotide kinase and washings were carried out in 6× SSC at 40° C.

After autoradiography, these oligonucleotides did not clearly reveal a specific DNA fragment. However, clonings were carried out and the clones, identified with the help of the oligonucleotides, did not contain the DNA fragments sought for after verification by nucleotide sequencing.

(4) Amplification of a DNA fragment of the beta toxin gene by PCR

Since the production of recombinant clones containing the beta toxin gene was not possible by conventional cloning methods, this gene was amplified by PCR. To do this, an oligonucleotide (P 279) deduced from the N-terminal protein sequence of the beta toxin and an oligonucleotide (P 280) deduced from an internal protein sequence (peptide 13) but in the reverse direction were used.

A DNA fragment of about 600 bp was thus amplified specifically from the total DNA of CWC 245.

The 600 bp DNA fragment was cloned in the pUC19 vector (pMRP 109 recombinant plasmid) and then sequenced. It contained an open reading framework and the terminal portions corresponded to the protein sequences obtained by protein microsequencing (N-terminal and peptide 13), showing that the cloned DNA fragment corresponded well to the gene sought for.

The 3' part of this gene was cloned in pUC 19 using the total DNA of CWC 245 digested by Sau 3A and identified with the P 311 marker whose sequence is localized in the 3' part of insert of pMRP 109. The pMRP 126 recombinant clone was sequenced and contained the stop codon of the beta toxin gene and a consensus transcription termination sequence. The sequence of the beta toxin gene from strain CWC 245 and its translation into amino acids are given in FIG. 3 SEQ ID NO:27.

(5) Comparison of the beta toxin gene from strain CWC 245 with that from strain NCTC 8533 and genetic analysis of the type C strains Titball et al (FEMS Microbiology Letters 97 (1992) 77–82) recently published the cloning and sequencing of the beta toxin gene from *C. perfringens* type B strain NCTC 8533.

Comparison of the protein sequence of the beta toxin from strain NCTC 8533 SEQ ID NO:28 (provisionally referred to as beta 1) with that of the beta toxin gene from strain CWC 245 SEQ ID NO:29 (provisionally referred to as beta 2) showed no significant homology (FIG. 4).

The role of beta toxin 2 as a virulence factor has not yet been clearly established.

The presence of the beta 1 and beta 2 genes was searched for by PCR in a series of type B and C *C. perfringens* strains (Table 1).

PCR conditions:

Buffer:

TRIS 10 mM pH 8.2

KCl 50 mM dNTP 100 mM

Bovine serum albumin 0.1 mg/ml

Beta-mercaptoethanol 10 mM

Primers 50 pmoles of each per reaction

TAQ polymerase (Amersham) 0.5$\mu$

Primers:

Primers for beta 2

SEQ ID NO:13 P319 5'-GGAAAGTGATGGAGAATTA TCTTAATGC-3'

SEQ ID NO:14 P320 5'-GCAGAATCAGGATTTTGA CCATATACC-3' (reverse)

573 bp amplified fragment.

Primers for beta 1

SEQ ID NO:15 BetatoxL 5'-AGGAGGTTTTTTT ATTTTTTTTTTTGAAG-3'

SEQ ID NO:16 BetatoxR 5'-TCTAAATAGC TGTTACTTTGTG-3'

962 bp amplified fragment.

Amplification cycles initial denaturation, 2 min at 94° C.

30 cycles comprising -20 s at 94° C.

20 s at 50° C.

20 s at 72° C.

5 minutes at 72° C.

PREM III thermocycler apparatus (Flobio)

Amplification products analysis by electrophoresis on 1% agar gel containing ethidium bromide and detection by UV transillumination.

These strains were identified by the standard method on mice using anti *C. perfringens* neutralizing serum (Welcome) according to the currently recognized nomenclature; all these strains produced the beta toxin.

Genetic analysis showed that the 3 B strains possessed the beta 1 gene and that the type C strains fell into 3 groups: those with the beta 1 gene, those with the beta 2 gene, and those with both (table 5).

The above experimental results show that the beta toxin gene from strain CMC245 differs from the beta toxin gene from strain NCTC 8533.

TABLE 1

Ability of duplex PCR to distinguish enterotoxigenic *C. perfringens* and *C. perfringens* between other Clostridium and other enterobacteria.

| Bacteria | Strain | PCR Result (1) |
|---|---|---|
| *Clostridium perfringens* type A | ATCC 13124 | + |
| *Clostridium perfringens* type B | CN39.22 | + |
| *Clostridium perfringens* type C | CWC 236 | + |
| *Clostridium perfringens* type D | 2534 | + |

TABLE 1-continued

Ability of duplex PCR to distinguish enterotoxigenic *C. perfringens* and *C. perfringens* between other Clostridium and other enterobacteria.

| Bacteria | Strain | PCR Result (1) |
|---|---|---|
| *Clostridium perfringens* type D | 250 | + |
| *Clostridium perfringens* type D | A0 | + |
| *Clostridium perfringens* type D | 48 | + |
| *Clostridium perfringens* type D | 76 | ++ |
| *Clostridium perfringens* type D | 64/1 | ++ |
| *Clostridium perfringens* type E | NCIB 1074S | ++ |
| *Clostridium perfringens* | 8 - 6 | ++ |
| *Clostridium perfringens* | 1088.0 | ++ |
| *Clostridium perfringens* | 4012 | ++ |
| *Clostridium perfringens* | 4086 | ++ |
| *Clostridium perfringens* | 4009 | + |
| *Clostridium perfringens* | 4010 | + |
| *Clostridium perfringens* | 4011 | + |
| *Clostridium perfringens* | 1089.1 | + |
| *Clostridium perfringens* | 1089.2 | + |
| *Clostridium perfringens* | 1089.3 | + |
| *Clostridium perfringens* | 1089.4 | + |
| *Clostridium perfringens* | 1089.5 | + |
| *Clostridium perfringens* | 1122 | + |
| *Clostridium perfringens* | 1513 | + |
| *Clostridium spiroformé* | 247 | – |
| *Clostridium subterminale* | ATCC 25774 | – |
| *Clostridium septicum* | ATCC 12464 | – |
| *Clostridium limosum* | 384 | – |
| *Clostridium beijerinckii* | VPI 5481 | – |
| *Clostridium mangenotii* | ATCC 25761 | – |
| *Clostridium chauvei* | IP 91 | – |
| *Bacillus thuringiensis* | 14001 | – |
| *Bacillus subtilis* | 168 | – |
| *Bacillus cereus* | LCHA 1203 | – |
| *Listeria monocytogenes* ½ a | A3 | – |
| *Listeria monocytogenes* ½ b | 13 | – |
| *Listeria monocytogenes* 4 b | 03 | – |
| *Listeria innocua* 6 a | C3 | – |
| *Listeria welshimeri* 6 h | E3 | – |
| *Listeria seeligeri* ½ b | D3 | – |
| *Clostridium botulinum* type A | ATCC 25763 | – |
| *Clostridium botulinum* type B | F 11 | – |
| *Clostridium botulinum* type C | 468 | – |
| *Clostridium botulinum* type D | 1873 | – |
| *Clostridium botulinum* type E | 9009 | – |
| *Clostridium botulinum* type F | NCIB 10658 | – |
| *Clostridium botulinum* type G | NCIB 10714 | – |
| *Clostridium baratii* (tox) | ATCC 27639 | – |
| *Clostridium baratii* (tox F) | ATCC 43756 | – |
| *Clostridium butyricum* (tox) | CB 25-1 | – |
| *Clostridium butyricum* (tox E) | ATCC 43181 | – |
| *Clostridium tetani* | E 19406 | – |
| *Clostridium sordellii* | IP 82 | – |
| *Clostridium bifermentans* | ATCC 638 | – |
| *Clostridium innoccuum* | NCIB 10674 | – |
| *Clostridium sporogenes* | ATCC 3584 | – |
| *Clostridium paraputrificum* | ATCC 25780 | – |
| *Clostridium difficile* | ATCC 9689 | – |
| *Clostridium difficile* | 203-1 | – |
| *Clostridium oedematiens* | ATCC 17861 | – |
| *Escherichia coli* 0: 157 H7 | LCHA P1 | – |
| *Escherichia coli* 0: 6 H16 | LCHA 877 | – |
| *Escherichia coli* 0: 125 B15 | LCHA 483 | – |
| *Salmonella typhimurium* | 3612 | – |
| *Salmonella enteritidis* | 3625 | – |
| *Salmonella agona* | 3628 | – |
| *Proteus sp* | 720S | – |
| *Kurthia sp* | C4 | – |
| *Pseudomonas aeruginosa* | 32 | – |
| *Staphylococcus aureus* | C3-0 | – |
| *Yersinia enterocolitica* | S31 | – |

(1) Symbols used for PCR results:
–: Négative reaction for alpha-toxin and enterotoxin genes.
+: Positive reaction for alpha-toxin gene.
++: Positive reaction for alpha-toxin and enterotoxin genes.

TABLE 2

| Stool samples investigation | | | |
|---|---|---|---|
| Samples | Number of sulfito-reductor bacteria | Duplex PCR | SLAT |
| 1 | $<10^4$ | – | – |
| 2 | $<10^4$ | – | – |
| 3 | $<10^4$ | – | – |
| 4 | $<10^4$ | + | – |
| 5 | $10^4$ | + | + |
| 6 | $10^4$ | + | + |
| 7 | $10^4$ | + | + |
| 8 | $2.10^4$ | + | + |
| 9 | $5.10^4$ | + | + |
| 10 | $5.10^4$ | + | + |
| 11 | $10^5$ | – | + |
| 12 | $10^5$ | + | + |
| 13 | $10^5$ | + | + |
| 14 | $2.10^5$ | – | – |
| 15 | $2.10^5$ | + | + |
| 16 | $8.10^5$ | + | + |
| 17 | $10^6$ | + | + |
| 18 | $2.10^6$ | + | + |
| 19 | $2.10^6$ | + | + |
| 20 | $10^7$ | + | + |
| 21 | $10^7$ | + | + |
| 22 | $10^7$ | + | + |
| 23 | $10^7$ | + | + |

TABLE 3

| C. perfringens investigation in food samples | | | | | |
|---|---|---|---|---|---|
| | C. perfringens investigation in naturally contaminated food samples | | | C. perfringens investigation in artificially contaminated food samples | |
| Food sample | Total | Classical method | Duplex PCR | Total | Duplex PCR |
| Cooked food | 31 | 1 ($5 \times 10^5$) | 1 | 30 | 30 |
| Pork butchery | 13 | 1 ($10^3$) | 1 | 12 | 12 |
| Raw meat | 11 | 0 | 0 | 11 | 11 |
| Milk product | 2 | 0 | 0 | 2 | 2 |
| Salad | 2 | 0 | 0 | 2 | 2 |

TABLE 4

Comparison between LS medium and the PCR technique in the detection of C. perfringens N = 44 animal foods (bone meal, meat or fish meal)

| | | LS MEDIUM (Beerens) | |
|---|---|---|---|
| | | + | – |
| PCR | + | 12 | 5* |
| | – | 3** | 24 |

*ASR concentration < 10/g

At least 1 colony identified as C. perfringens after isolation on TSC medium.

**No colony isolated on TSC medium was identified as C. perfringens.

TABLE 5

PCR identification of the genes for beta toxin 1 sequenced from strain NCTC 8533 and beta toxin 2 sequenced from strain CWC 245 in different strains of type B and C C. perfringens identified by the standard method

| | Beta 1 | Beta 2 |
|---|---|---|
| C. perfringens B | | |
| NCTC8533 | + | – |
| NCTC6121 | + | – |
| IP278-220 | + | – |
| CN3922 | + | – |
| C. perfringens C | | |
| ATCC3628 | + | – |
| NCTC8081 | + | – |
| NCTC3180 | + | + |
| NCTC3182 | + | + |
| NR866 | + | + |
| NR316 | + | + |
| CWC236 | + | + |
| CWC239 | + | + |
| CWC240 | + | + |
| CWC241 | + | + |
| CWC243 | + | + |
| IP232-87 | + | + |
| IP692-83 | + | + |
| CWC235 | – | + |
| CWC237 | – | + |
| CWC245 | – | + |
| CWC249 | – | + |
| S608 | – | + |
| IP93R | – | + |

SEQUENCE LISTING ( 1 ) GENERAL INFORMATION:

( i i i ) NUMBER OF SEQUENCES: 29

( 2 ) INFORMATION FOR SEQ ID NO: 1:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO: 1:

AAGTTACCTT TGCTGCATAA TCCC 24

( 2 ) INFORMATION FOR SEQ ID NO: 2:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 2:

A T A G A T A C T C   C A T A T C A T C C   T G C T   2 4

( 2 ) INFORMATION FOR SEQ ID NO: 3:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 3:

T C A A A A G A A T   A T G C A A G A G G   T   2 1

( 2 ) INFORMATION FOR SEQ ID NO: 4:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 4:

T T C T A T C T T G   G A G A G G C T A T   G C A C   2 4

( 2 ) INFORMATION FOR SEQ ID NO: 5:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 5:

G C T A C T A G T T   C T T T T A C A T T   C T T T C C   2 6

( 2 ) INFORMATION FOR SEQ ID NO: 6:

( i ) SEQUENCE CHARACTERISTICS:
( A ) LENGTH: 29 base pairs
( B ) TYPE: nucleic acid
( C ) STRANDEDNESS: single

```
( D ) TOPOLOGY: linear

( i i i ) HYPOTHETICAL: NO

( v i ) ORIGINAL SOURCE:
( A ) ORGANISM: Clostridium perfringens

( x i ) SEQUENCE DESCRIPTION: SEQ ID NO: 6:

GAAAGATCTG TATCTACAAC TGCTGGTCC                                    29

( 2 ) INFORMATION FOR SEQ ID NO: 7:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear

( i i i ) HYPOTHETICAL: NO

( v i ) ORIGINAL SOURCE:
( A ) ORGANISM: Clostridium perfringens

( x i ) SEQUENCE DESCRIPTION: SEQ ID NO: 7:

GCTGGCTAAG ATTCTATATT TTTGTCCAGT                                   30

( 2 ) INFORMATION FOR SEQ ID NO: 8:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear

( i i i ) HYPOTHETICAL: NO

( v i ) ORIGINAL SOURCE:
( A ) ORGANISM: Clostridium perfringens

( x i ) SEQUENCE DESCRIPTION: SEQ ID NO: 8:

GAACGCCAAT CATATAAATT TCCAGCTGGG                                   30

( 2 ) INFORMATION FOR SEQ ID NO: 9:

( i ) SEQUENCE CHARACTERISTICS:
( A ) LENGTH: 677 base pairs
( B ) TYPE: nucleic acid
( C ) STRANDEDNESS: single
( D ) TOPOLOGY: linear

( i i i ) HYPOTHETICAL: NO

( v i ) ORIGINAL SOURCE:
( A ) ORGANISM: Clostridium perfringens

( i x ) FEATURE:
( A ) NAME/KEY: CDS
( B ) LOCATION:1..676

( x i ) SEQUENCE DESCRIPTION: SEQ ID NO: 9:

AAA GAA ATG GAT GCG TAT AGG AAA GTG ATG GAG AAT                    36
Lys Glu Met Asp Ala Tyr Arg Lys Val Met Glu Asn
  1                 5                  10

TAT CTT AAT GCT TTA AAA AAC TAC GAT ATT AAT ACA                    72
Tyr Leu Asn Ala Leu Lys Asn Tyr Asp Ile Asn Thr
        15                  20

GTT GTA AAC ATT TCA GAA GAT GAA AGA GTA AAT AAT                   108
Val Val Asn Ile Ser Glu Asp Glu Arg Val Asn Asn
25                  30                  35
```

-continued

GTT GAA CAG TAT AGA GAA ATG TTA GAA GAT TTT AAA 144
Val Glu Gln Tyr Arg Glu Met Leu Glu Asp Phe Lys
40 45

TAT GAT CCT AAC CAA CAA CTG AAA TCT TTT GAA ATA 180
Tyr Asp Pro Asn Gln Gln Leu Lys Ser Phe Glu Ile
50 55 60

CTT AAT TCA CAA AAG AGC GAT AAT AAA GAA ATA TTT 216
Leu Asn Ser Gln Lys Ser Asp Asn Lys Glu Ile Phe
65 70

AAT GTA AAA ACT GAA TTT TTA AAT GGT GCA ATT TAT 252
Asn Val Lys Thr Glu Phe Leu Asn Gly Ala Ile Tyr
75 80

GAT ATG GAA TTT ACT GTA TCA TCT AAA GAT GGA AAA 288
Asp Met Glu Phe Thr Val Ser Ser Lys Asp Gly Lys
85 90 95

TTA ATA GTA TCT GAT ATG GAA AGA ACA AAA GTT GAG 324
Leu Ile Val Ser Asp Met Glu Arg Thr Lys Val Glu
100 105

AAT GAA GGA AAA TAT ATT TTA ACA CCA TCA TTT AGA 360
Asn Glu Gly Lys Tyr Ile Leu Thr Pro Ser Phe Arg
110 115 120

ACT CAA GTT TGT ACA TGG GAT GAT GAA CTA GCA CAA 396
Thr Gln Val Cys Thr Trp Asp Asp Glu Leu Ala Gln
125 130

GCA ATT GGG GGA GTT TAT CCA CAA ACA TAT TCT GAT 432
Ala Ile Gly Gly Val Tyr Pro Gln Thr Tyr Ser Asp
135 140

AGA TTT ACA TAT TAT GCA GAT AAT ATA TTA TTA AAC 468
Arg Phe Thr Tyr Tyr Ala Asp Asn Ile Leu Leu Asn
145 150 155

TTC AGA CAA TAT GCA ACT TCA GGT TCA AGA GAT TTA 504
Phe Arg Gln Tyr Ala Thr Ser Gly Ser Arg Asp Leu
160 165

AAA GTA GAA TAT AGT GTT GTA GAT CAT TGG ATG TGG 540
Lys Val Glu Tyr Ser Val Val Asp His Trp Met Trp
170 175 180

AAA GAT GAT GTT AAA GCT TCT CAA ATG GTA TAT GGT 576
Lys Asp Asp Val Lys Ala Ser Gln Met Val Tyr Gly
185 190

CAA AAT CCT GAT TCT GCT AGA CAA ATA AGA TTA TAT 612
Gln Asn Pro Asp Ser Ala Arg Gln Ile Arg Leu Tyr
195 200

ATA GAA AAA GGA CAA TCT TTC TAT AAA TAT AGA ATA 648
Ile Glu Lys Gly Gln Ser Phe Tyr Lys Tyr Arg Ile
205 210 215

AGA ATT AAA AAC TTT ACA CCT GCA TCA AT 677
Arg Ile Lys Asn Phe Thr Pro Ala Ser
220 225

( 2 ) INFORMATION FOR SEQ ID NO: 10:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( i x ) FEATURE:
( D ) OTHER INFORMATION: modified bases at postions 9, 15, 21 and 27 are inosine.

( x i ) SEQUENCE DESCRIPTION: SEQ ID NO: 10:

AAAGAAATNG ATGCNTATAG NAAAGTNATG G 31

( 2 ) INFORMATION FOR SEQ ID NO: 11:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( i x ) FEATURE:
( D ) OTHER INFORMATION: modified base at positions 3, 6, 9 and 12 are inosine ( x i ) SEQUENCE DESCRIPTION: SEQ ID NO: 11:

ATNGANGCNG GNGTAAAATT 20

( 2 ) INFORMATION FOR SEQ ID NO: 12:

( i ) SEQUENCE CHARACTERISTICS:
( A ) LENGTH: 357 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( i x ) FEATURE:
( A ) NAME/KEY: pMRP126

( x i ) SEQUENCE DESCRIPTION: SEQ ID NO: 12:

```
GAT CAT TGG ATG TGG AAA GAT GAT GTT AAA GCT TCT     36
Asp His Trp Met Trp Lys Asp Asp Val Lys Ala Ser
 1               5                  10

CAA ATG GTA TAT GGT CAA AAT CCT GAT TCT GCT AGA     72
Gln Met Val Tyr Gly Gln Asn Pro Asp Ser Ala Arg
         15                  20

CAA ATA AGA TTA TAT ATA GAA AAA GGA CAA TCT TTC    108
Gln Ile Arg Leu Tyr Ile Glu Lys Gly Gln Ser Phe
 25                  30                  35

TAT AAA TAT AGA ATA AGA ATT AAA AAC TTT ACA CCT    144
Tyr Lys Tyr Arg Ile Arg Ile Lys Asn Phe Thr Pro
             40                  45

GCA TCA ATT AGA GTA TTT GGT GAA GGG TAT TGT GCA    180
Ala Ser Ile Arg Val Phe Gly Glu Gly Tyr Cys Ala
     50                  55                  60

T AGAAAAAAT ATGAAGTGAC TTAGTCACTT CATATTTTTT       221

TTACTATTAA TTTTATTATA TAAAAACCTA ACATACATGA        261

AAGTATTCTT AATACAGTTA TATCAAAATT AAAGTAGGGG        301

AAATAAAATA AAAGGCTAAA AACTATATTA AAAACTATAA        341

AAATTATTAA ATTAGG                                  357
```

( 2 ) INFORMATION FOR SEQ ID NO: 13:

-continued ( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 13:

GGAAAGTGAT GGAGAATTAT CTTAATGC 28

( 2 ) INFORMATION FOR SEQ ID NO: 14:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 14:

GCAGAATCAG GATTTTGACC ATATACC 27

( 2 ) INFORMATION FOR SEQ ID NO: 15:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 15:

AGGAGGTTTT TTTATTTTTT TTTTTGAAG 29

( 2 ) INFORMATION FOR SEQ ID NO: 16:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 16:

TCTAAATAGC TGTTACTTTG TG 22

( 2 ) INFORMATION FOR SEQ ID NO: 17:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 17:

Asn Tyr Asp Ile Asn Thr Val Val Asn Ile Ser Glu Asp
1 5 10

Glu ( 2 ) INFORMATION FOR SEQ ID NO: 18:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( i x ) FEATURE:
( D ) OTHER INFORMATION: the modified bases at positions 9, 15, 18, 21, 27 and 30 are inosine ( x i ) SEQUENCE DESCRIPTION: SEQ ID NO: 18:

TATGATATNA ATACNGTNGT NAATATNTCN GAAGATGAA 39

( 2 ) INFORMATION FOR SEQ ID NO: 19:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 19:

Val Met Glu Asn Tyr Leu Asn Ala Leu Lys Tyr Ile
1 5 10

Leu Thr Pro Ser Phe
15

( 2 ) INFORMATION FOR SEQ ID NO: 20:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( i x ) FEATURE:
( D ) OTHER INFORMATION: modified bases at positions 3, 18, 24 and 27 are inosine ( x i ) SEQUENCE DESCRIPTION: SEQ ID NO: 20:

GTNATGGAAA ATTATTTNAA TGCNTTNAAA 30

( 2 ) INFORMATION FOR SEQ ID NO: 21:

-continued ( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( i x ) FEATURE:
( D ) OTHER INFORMATION: modified bases at positions 3, 18, 24 and 27 are inosine ( x i ) SEQUENCE DESCRIPTION: SEQ ID NO: 21:

CANTACCTTT TAATAAANTT ACGNAANTT 29

( 2 ) INFORMATION FOR SEQ ID NO: 22:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 22:

Lys Glu Ile Asp Ala Tyr Arg Lys Val Met Glu Asn
1 5 10

Tyr Leu Asn Ala Leu
15

( 2 ) INFORMATION FOR SEQ ID NO: 23:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( i x ) FEATURE:
( D ) OTHER INFORMATION: modified bases at positions 9, 15, 21, 27 and 42 are inosine ( x i ) SEQUENCE DESCRIPTION: SEQ ID NO: 23:

AAAGAAATNG ATGCNTATAG NAAAGTNATG GAAAATTATT 40

TNAATGC 47

( 2 ) INFORMATION FOR SEQ ID NO: 24:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 24:

Asn Phe Thr Pro Ala Ser Ile
1 5

( 2 ) INFORMATION FOR SEQ ID NO: 25:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( i x ) FEATURE:
( D ) OTHER INFORMATION: modified bases at positions 6, 9, 12, 15 and 18 are inosine ( x i ) SEQUENCE DESCRIPTION: SEQ ID NO: 25:

AATTTNACNC CNGCNTCNAT 20

( 2 ) INFORMATION FOR SEQ ID NO: 26:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( i x ) FEATURE:
( D ) OTHER INFORMATION: modified base at positions 9, 12, 15 and 18 are inosine ( x i ) SEQUENCE DESCRIPTION: SEQ ID NO: 26:

TTAAAATGNG GNCGNAGNTA 20

( 2 ) INFORMATION FOR SEQ ID NO: 27:

( i ) SEQUENCE CHARACTERISTICS:
( A ) LENGTH: 882 base pairs
( B ) TYPE: nucleic acid
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( i x ) FEATURE:
( A ) NAME/KEY: beta 2

( x i ) SEQUENCE DESCRIPTION: SEQ ID NO: 27:

AAA GAA ATG GAT GCG TAT AGG AAA GTG ATG GAG AAT 36
Lys Glu Met Asp Ala Tyr Arg Lys Val Met Glu Asn
1 5 10

TAT CTT AAT GCT TTA AAA AAC TAC GAT ATT AAT ACA 72
Tyr Leu Asn Ala Leu Lys Asn Tyr Asp Ile Asn Thr
15 20

GTT GTA AAC ATT TCA GAA GAT GAA AGA GTA AAT AAT 108
Val Val Asn Ile Ser Glu Asp Glu Arg Val Asn Asn
25 30 35

GTT GAA CAG TAT AGA GAA ATG TTA GAA GAT TTT AAA 144

-continued

```
Val Glu Gln Tyr Arg Glu Met Leu Glu Asp Phe Lys
            40                  45

TAT GAT CCT AAC CAA CAA CTG AAA TCT TTT GAA ATA          180
Tyr Asp Pro Asn Gln Gln Leu Lys Ser Phe Glu Ile
    50                  55                  60

CTT AAT TCA CAA AAG AGC GAT AAT AAA GAA ATA TTT          216
Leu Asn Ser Gln Lys Ser Asp Asn Lys Glu Ile Phe
                65                  70

AAT GTA AAA ACT GAA TTT TTA AAT GGT GCA ATT TAT          252
Asn Val Lys Thr Glu Phe Leu Asn Gly Ala Ile Tyr
        75                  80

GAT ATG GAA TTT ACT GTA TCA TCT AAA GAT GGA AAA          288
Asp Met Glu Phe Thr Val Ser Ser Lys Asp Gly Lys
85                  90                  95

TTA ATA GTA TCT GAT ATG GAA AGA ACA AAA GTT GAG          324
Leu Ile Val Ser Asp Met Glu Arg Thr Lys Val Glu
            100                 105

AAT GAA GGA AAA TAT ATT TTA ACA CCA TCA TTT AGA          360
Asn Glu Gly Lys Tyr Ile Leu Thr Pro Ser Phe Arg
    110                 115                 120

ACT CAA GTT TGT ACA TGG GAT GAT GAA CTA GCA CAA          396
Thr Gln Val Cys Thr Trp Asp Asp Glu Leu Ala Gln
                125                 130

GCA ATT GGG GGA GTT TAT CCA CAA ACA TAT TCT GAT          432
Ala Ile Gly Gly Val Tyr Pro Gln Thr Tyr Ser Asp
        135                 140

AGA TTT ACA TAT TAT GCA GAT AAT ATA TTA TTA AAC          468
Arg Phe Thr Tyr Tyr Ala Asp Asn Ile Leu Leu Asn
145                 150                 155

TTC AGA CAA TAT GCA ACT TCA GGT TCA AGA GAT TTA          504
Phe Arg Gln Tyr Ala Thr Ser Gly Ser Arg Asp Leu
            160                 165

AAA GTA GAA TAT AGT GTT GTA GAT CAT TGG ATG TGG          540
Lys Val Glu Tyr Ser Val Val Asp His Trp Met Trp
    170                 175                 180

AAA GAT GAT GTT AAA GCT TCT CAA ATG GTA TAT GGT          576
Lys Asp Asp Val Lys Ala Ser Gln Met Val Tyr Gly
                185                 190

CAA AAT CCT GAT TCT GCT AGA CAA ATA AGA TTA TAT          612
Gln Asn Pro Asp Ser Ala Arg Gln Ile Arg Leu Tyr
        195                 200

ATA GAA AAA GGA CAA TCT TTC TAT AAA TAT AGA ATA          648
Ile Glu Lys Gly Gln Ser Phe Tyr Lys Tyr Arg Ile
205                 210                 215

AGA ATT AAA AAC TTT ACA CCT GCA TCA ATT AGA GTA          684
Arg Ile Lys Asn Phe Thr Pro Ala Ser Ile Arg Val
            220                 225

TTT GGT GAA GGG TAT TGT GCA T AGAAAAAAAT                 716
Phe Gly Glu Gly Tyr Cys Ala
    230                 235

ATGAAGTGAC TTAGTCACTT CATATTTTTT TTACTATTAA              756

TTTTATTATA TAAAAACCTA ACATACATGA AAGTATTCTT              796

AATACAGTTA TATCAAAATT AAAGTAGGGG AAATAAAATA              836

AAAGGCTAAA AACTATATTA AAAACTATAA AAATTATTAA              876

ATTAGC                                                   882
```

( 2 ) INFORMATION FOR SEQ ID NO: 28:

-continued ( i ) SEQUENCE CHARACTERISTICS:
( A ) LENGTH: 336 amino acids
( B ) TYPE: amino acids
( C ) STRANDEDNESS: single
( D ) TOPOLOGY: linear ( i i i ) HYPOTHETICAL: NO ( v i ) ORIGINAL SOURCE:
( A ) ORGANISM: Clostridium perfringens ( i x ) FEATURE:
( A ) NAME/KEY: beta 1

( x i ) SEQUENCE DESCRIPTION: SEQ ID NO: 28:

```
Met Lys Lys Lys Phe Ile Ser Leu Val Ile Val Ser
  1             5                      10

Ser Leu Leu Asn Gly Cys Leu Leu Ser Pro Thr Leu
         15                  20

Val Tyr Ala Asn Asp Ile Gly Lys Thr Thr Thr Ile
 25                  30                  35

Thr Arg Asn Lys Thr Ser Asp Gly Tyr Thr Ile Ile
             40                  45

Thr Gln Asn Asp Lys Gln Ile Ile Ser Tyr Gln Ser
     50                  55                  60

Val Asp Ser Ser Ser Lys Asn Glu Asp Gly Phe Thr
                 65                  70

Ala Ser Ile Asp Ala Arg Phe Ile Asp Asp Lys Tyr
         75                  80

Ser Ser Glu Met Thr Thr Leu Ile Asn Leu Thr Gly
 85                  90                  95

Phe Met Ser Ser Lys Lys Glu Asp Val Ile Lys Lys
            100                 105

Tyr Asn Leu His Asp Val Thr Asn Ser Thr Ala Ile
    110                 115                 120

Asn Phe Pro Val Arg Tyr Ser Ile Ser Ile Leu Asn
                125                 130

Glu Ser Ile Asn Glu Asn Val Lys Ile Val Asp Ser
        135                 140

Ile Pro Lys Asn Thr Ile Ser Gln Lys Thr Val Ser
145                 150                 155

Asn Thr Met Gly Tyr Lys Ile Gly Gly Ser Ile Glu
            160                 165

Ile Glu Glu Asn Lys Pro Lys Ala Ser Ile Glu Ser
    170                 175                 180

Glu Tyr Ala Glu Ser Ser Thr Ile Glu Tyr Val Gln
                185                 190

Pro Asp Phe Ser Thr Ile Gln Thr Asp His Ser Thr
        195                 200

Ser Lys Ala Ser Trp Asp Thr Lys Phe Thr Glu Thr
205                 210                 215

Thr Arg Gly Asn Tyr Asn Leu Lys Ser Asn Asn Pro
            220                 225

Val Tyr Gly Asn Glu Met Phe Met Tyr Gly Arg Tyr
    230                 235                 240

Thr Asn Val Pro Ala Thr Glu Asn Ile Ile Pro Asp
                245                 250

Tyr Gln Met Ser Lys Leu Ile Thr Gly Gly Leu Asn
```

-continued 255 260

Pro Asn Met Ser Val Val Leu Thr Ala Pro Asn Gly
265 270 275

Thr Glu Glu Ser Ile Ile Lys Val Lys Met Glu Arg
280 285

Glu Arg Asn Cys Tyr Tyr Leu Asn Trp Asn Gly Ala
290 295 300

Asn Trp Val Gly Gln Val Tyr Ser Arg Leu Ala Phe
305 310

Asp Thr Pro Asn Val Asp Ser His Ile Phe Thr Phe
315 320

Lys Ile Asn Trp Leu Thr His Lys Val Thr Ala Ile
325 330 335

( 2 ) INFORMATION FOR SEQ ID NO: 29:

( i ) SEQUENCE CHARACTERISTICS:
( A ) LENGTH: 225 amino acids
( B ) TYPE: amino acid
( D ) TOPOLOGY: linear ( i x ) FEATURE:
( A ) NAME/KEY: beta 2

( x i ) SEQUENCE DESCRIPTION: SEQ ID NO: 29:

Lys Glu Met Asp Ala Tyr Arg Lys Val Met Glu Asn
1 5 10

Tyr Leu Asn Ala Leu Lys Asn Tyr Asp Ile Asn Thr
15 20

Val Val Asn Ile Ser Glu Asp Glu Arg Val Asn Asn
25 30 35

Val Glu Gln Tyr Arg Glu Met Leu Glu Asp Phe Lys
40 45

Tyr Asp Pro Asn Gln Gln Leu Lys Ser Phe Glu Ile
50 55 60

Leu Asn Ser Gln Lys Ser Asp Asn Lys Glu Ile Phe
65 70

Asn Val Lys Thr Glu Phe Leu Asn Gly Ala Ile Tyr
75 80

Asp Met Glu Phe Thr Val Ser Ser Lys Asp Gly Lys
85 90 95

Leu Ile Val Ser Asp Met Glu Arg Thr Lys Val Glu
100 105

Asn Glu Gly Lys Tyr Ile Leu Thr Pro Ser Phe Arg
110 115 120

Thr Gln Val Cys Thr Trp Asp Asp Glu Leu Ala Gln
125 130

Ala Ile Gly Gly Val Tyr Pro Gln Thr Tyr Ser Asp
135 140

Arg Phe Thr Tyr Tyr Ala Asp Asn Ile Leu Leu Asn
145 150 155

Phe Arg Gln Tyr Ala Thr Ser Gly Ser Arg Asp Leu
160 165

Lys Val Glu Tyr Ser Val Val Asp His Trp Met Trp
170 175 180

Lys Asp Asp Val Lys Ala Ser Gln Met Val Tyr Gly
185 190

-continued

| | | | | | | | | | | | |
|---|---|---|---|---|---|---|---|---|---|---|---|
| Gln | Asn | Pro<br>195 | Asp | Ser | Ala | Arg | Gln<br>200 | Ile | Arg | Leu | Tyr |
| Ile<br>205 | Glu | Lys | Gly | Gln | Ser<br>210 | Phe | Tyr | Lys | Tyr | Arg<br>215 | Ile |
| Arg | Ile | Lys | Asn<br>220 | Phe | Thr | Pro | Ala | Ser<br>225 | | | |

What we claim is:

1. An isolated nucleic acid encoding the *C. perfringens* type beta toxin β2 consisting of the nucleotide sequence of SEQ ID No. 27.

2. The plasmids of the gene of claim 1 deposited in CNCM collection under reference I-1499 and I-1500.

3. A process for the detection of the gene encoding lecithinase in a sample comprising isolating DNA from the sample, amplifying parts of the gene encoding lecithinase by chain polymerization with a primer selected from the group consisting of SEQ ID Nos. 1–4 and 5 and detecting the amplification products.

4. A process for the detection of the gene encoding enterotoxin in a sample comprising isolating DNA from the sample, amplifying parts of the gene encoding enterotoxin by chain polymerization with a primer selected from the group consisting of SEQ ID. Nos. 6, 7 and 8 and detecting the amplification products.

* * * * *